United States Patent [19]
Kolpak

[11] Patent Number: 5,218,840
[45] Date of Patent: Jun. 15, 1993

[54] DETERMINING COMPRESSIBILITY FACTORS FOR MULTIPHASE FLUID FLOW MEASUREMENT SYSTEM

[75] Inventor: Miroslav M. Kolpak, Plano, Tex.

[73] Assignee: Atlantic Richfield Company, Los Angeles, Calif.

[21] Appl. No.: 772,994

[22] Filed: Oct. 8, 1991

[51] Int. Cl.$^5$ .......................................... G01N 33/28
[52] U.S. Cl. ............................................. 73/61.44
[58] Field of Search ................................. 73/61.44

[56] References Cited

U.S. PATENT DOCUMENTS

| | | | |
|---|---|---|---|
| 3,911,256 | 10/1975 | Jones | 73/61.44 |
| 4,852,395 | 8/1989 | Kolpak | 73/61.44 |
| 4,924,695 | 5/1990 | Kolpak | 73/61.44 |

Primary Examiner—Hezron E. Williams
Assistant Examiner—Joseph W. Roskos
Attorney, Agent, or Firm—Michael E. Martin

[57] ABSTRACT

The compressibility coefficient of liquid compositions in a liquid mixture are measured with a system comprising a separator vessel and a vessel forming a closable variable volume chamber. A quantity of liquid mixture is trapped in the chamber and the volume is reduced while measuring the pressure increase to determine the compressibility coefficient of a quantity of the liquid mixture. An incremental volume of one of the liquid component compositions is added to the liquid mixture in the chamber and the compressibility coefficient of the new liquid mixture is measured to determine the compressibility coefficient of the liquid component of the incremental volume. The compressibility factor of gas in the liquid mixture may also be determined by compressing a quantity of the gas and fitting a polynomial equation to the pressure-volume relationship.

10 Claims, 2 Drawing Sheets

DETERMINING COMPRESSIBILITY FACTORS FOR MULTIPHASE FLUID FLOW MEASUREMENT SYSTEM

BACKGROUND OF THE INVENTION

1. Field of the Invention

The present invention pertains to determining the compressibility factors for gas and liquid components of a multiphase fluid flowstream for use in determining the gas and liquid component fractions of the fluid.

2. Background

My U.S. Pat. No. 4,852,395 issued Aug. 1, 1989 and assigned to the assignee of the present invention describes a multi-phase fluid flow measuring system wherein, in particular, a mixture of gas, oil and water is acted on to determine the gas fraction and the oil and water fractions, respectively. The methodology associated with the system described in the patent requires the determination of a gas compressibility factor and the compressibility coefficients of the respective liquid components of the liquid phase of the fluid. Although a "one-time" or infrequent determination of these factors may be sufficient for some metering applications, it is advantageous to more frequently determine these compressibility coefficients due to changing compositions of the fluids being metered so as to more accurately determine the various fluid component fractions of the overall fluid flowstream. The present invention provides a solution to this problem.

SUMMARY OF THE INVENTION

The present invention provides a method and system for determining the compressibility factors of the fluid components of a multiphase fluid flowstream, in particular, a fluid flowstream comprising gas, oil and water.

In accordance with an important aspect of the present invention, the liquid compressibility coefficients for a liquid mixture having at least two generally immiscible liquids, such as oil and water, may be determined by measuring the liquid compressibility of a first quantity of a liquid mixture, while measuring the gas fraction of the first quantity to determine the liquid volume of the total quantity, then adding an incremental volume of a liquid of unknown compressibility to the previous batch or quantity, then measuring the liquid compressibility of the second quantity and then determining the compressibility of the liquid in the incremental volume.

In accordance with another aspect of the present invention, the compressibility factor for the gas being measured by the method of the present invention may also be determined utilizing a multiphase flow measurement system generally of the type described in U.S. Pat. No. 4,852,395, which may be modified by the invention in U.S. Pat. No. 4,924,695, both assigned to the assignee of the present invention.

Still further, the present invention provides a system generally of the type described in the aforementioned patents which has been modified to provide for sampling the liquid components of a liquid mixture and sampling the gas component of a multiphase liquid and gas mixture.

Those skilled in the art will further appreciate the above-described features and advantages of the present invention together with other superior aspects thereof upon reading the detailed description which follows in conjunction with the drawing.

DESCRIPTION OF PREFERRED EMBODIMENTS

Figure 1:
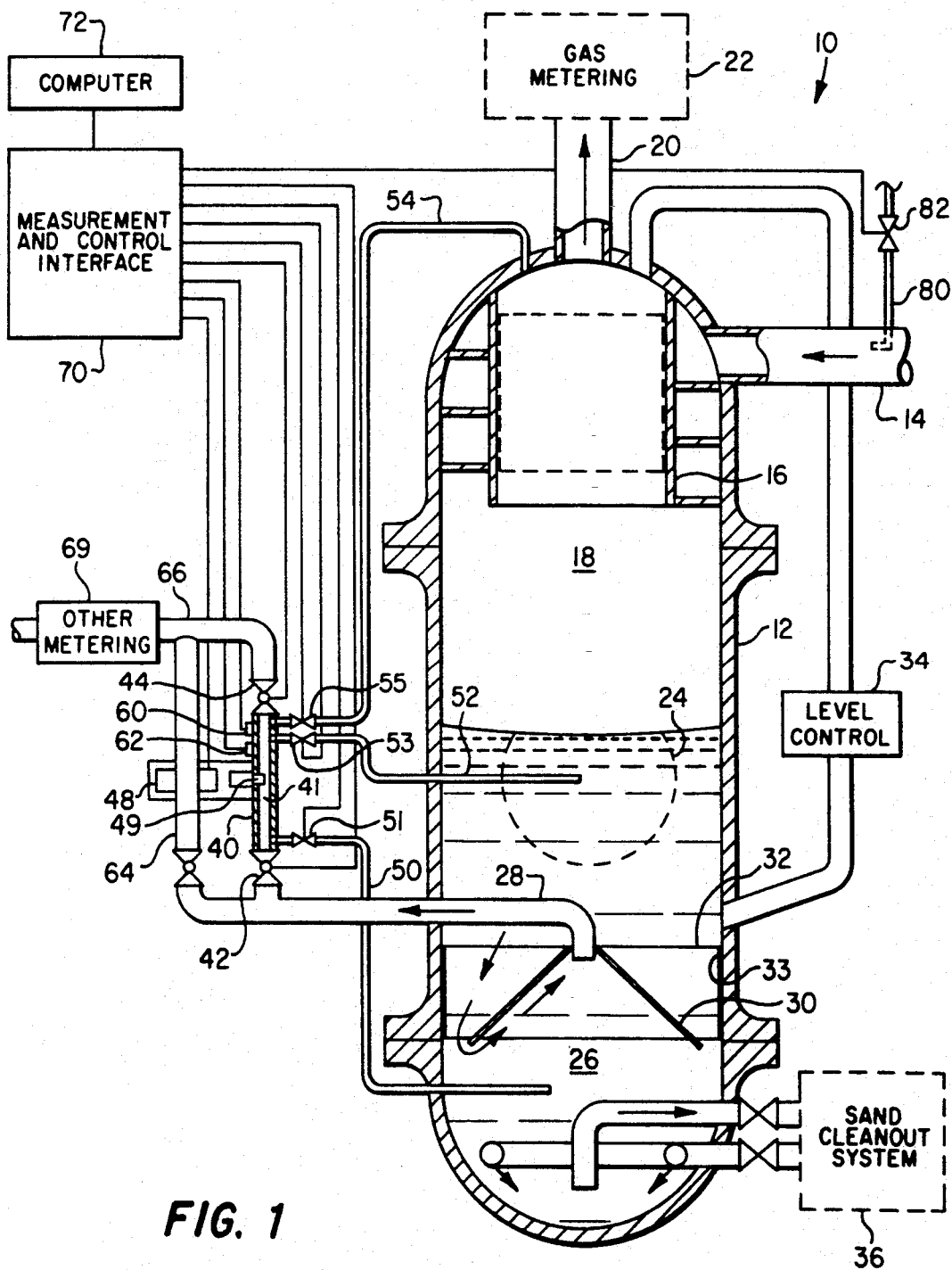
FIG. 1 is a schematic diagram of one embodiment of a system for determining the compressibility factors in accordance with the present invention.

In the description which follows, like elements are marked throughout the specification and drawing with the same reference numerals, respectively.

Referring to FIG. 1 there is illustrated a multiphase fluid flow measurement system in accordance with the present invention and generally designated by the numeral 10. The system 10 is similar to that described in U.S. Pat. No. 4,852,395 and for the sake of description of the system 10, the subject matter of U.S. Pat. No. 4,852,395 is incorporated herein by reference. The system 10 includes a separator vessel 12 for receiving a multiphase fluid flow mixture from an inlet conduit 14, which mixture is separated into liquid and gas components by a centrifugal separator part 16. Gas separated from the liquid component of the mixture collects in a chamber 18 and flows through a gas discharge conduit 20 to a gas metering device 22.

The system 10, as with the system described in U.S. Pat. No. 4,852,395, is particularly adapted for measuring the flow rate of a mixture of gas, crude oil and water typically resulting from production from oil or gas wells. Certain other liquids such as condensates and natural gasoline may be present in the liquid mixture but crude oil and water are the primary liquid components. The liquid collects in the vessel 12 below the space 18 and tends to separate into oil and water fractions. For example, the oil fraction would tend to collect within a zone 24 indicated in FIG. 1 while water would tend to settle to the bottom of the vessel 12 in a space generally designated by the numeral 26. Liquid is withdrawn from the vessel 12 through a discharge conduit 28.

The vessel 12 is preferably modified to have a so-called vortex breaker formed therein and comprising a conical-shaped baffle 30 and generally vertically extending anti-swirl baffles 32 extending between the baffle 30 and the interior side wall 33 of the vessel 12. A suitable level control device may be included in the system 10 as indicated as 34. Moreover, debris such as sand and other solids entrained in the liquid flowstream may be extracted from the bottom of the interior of the vessel 12 by a suitable sand cleanout system 36, preferably of the type described in U.S. Pat. No. 4,913,819 issued Apr. 3, 1990 to John C. Patterson and assigned to the assignee of the present invention.

The discharge conduit 28 is connected to a so-called batch sampler, generally designated by the numeral 40, which is closable at its opposite ends by remotely controlled valves 42 and 44. The batch sampler 40 may be a generally cylindrical tubular conduit closable by the valves 42 and 44 and adapted to have the volume of its interior chamber 41 changed by a controlled piston-type actuator generally designated by the numeral 48. Accordingly, a quantity of fluid may be trapped in the batch sampler 40 and the volume of that fluid may be changed incrementally by the extending and retracting the piston 49 of actuator 48 with respect to the chamber 41 to vary its volume. A more detailed description of the sampler or device 40 is described in U.S. Pat. No. 4,852,395. An alternate embodiment of the batch sampler which comprises a flexible sleeve device is described in U.S. Pat. No. 4,924,695. The '695 patent is also incorporated herein by reference with respect to the description of the devices for sampling a volume of fluid. Accordingly, further detailed description of the batch sampler 40 is not believed to be necessary to practice the present invention. The chamber 41 may also receive fluid by way of a conduit 50 from the space 26 of the vessel 12, or by way of a conduit 52 from the area or zone 24 which includes the separated oil, or by way of a conduit 54 which is operable to conduct gas to the chamber 41. The conduits 50, 52 and 54 are closable by remotely controlled valves 51, 53, and 55 respectively. Pressure and temperature sensors 60 and 62 are also in communication with the chamber 41 for determining the pressure and temperature, respectively, of a fluid sample trapped in the chamber.

The system 10 includes a bypass conduit 64 which is in communication with a conduit 66 for conducting fluid from the discharge conduit 28 to other metering devices 69 during sampling of the fluid and practicing the method of the present invention. The valves 42, 44, 51, 53, 55, the actuator 48 and the sensors 60 and 62 may all be controlled through a measurement and control interface 70 which is suitably connected to a computer 72. Accordingly, the method described below may be automated and calculations of the compressibility coefficients carried out utilizing conventional practice in the art of process measurement and control.

Determination of the compressibility coefficient for a liquid such as oil which has separated and collected in the zone 24 of the vessel 12 as well as the compressibility coefficient of the more dense liquid, such as water, which has collected in the space 26 may be determined in accordance with the following procedure. The liquid compressibility coefficient of a mixed liquid may be measured by trapping a sample of the liquid in the chamber 41 between the valves 42 and 44 and operating the actuator 48 to change the volume of the chamber 41 whereupon the gas fraction (fg1) and the liquid mixture compressibility coefficient (b1) may be measured in accordance with the procedure described in U.S. Pat. No. 4,852,395. Simultaneously, the liquid volume (V) of the total volume (V,)of the sample or "batch 1" in the chamber 41 is determined.

A volume dV of liquid "x", of unknown compressibility (bx) is added to the previous quantity or volume V. Then the liquid compressibility (bm2) of the resulting is measured (now having a volume of V+dV); the "2" in bm2 implies "batch 2". The variables are defined as follows: (o, w, x) imply, respectively, (oil, water, liquid x)

| $(bo, bw, bx)$ | = | liquid compressibilities | |
| --- | --- | --- | --- |
| $(Vo1, Vw1)$ | = | liquid volumers in batch 1 | (1) |
| $V$ | = | $Vo1 + Vw1$ | |
| $(fo1, fw1)$ | = | liquid fractions in batch 1 | (2) |
| | = | $Vo1/V$ and $Vw1/V$, respectively | |
| $V + dv$ | = | volume of liquid in batch 2 | (3) |
| | = | $Vo1 + Vw1 + dV$ | |

The batch 1 liquids, expressed as fractions of the batch 2 volume, are

| $(fo2, fw2)$ | = | batch 1 liquid fractions in batch 2 | (4) |
| --- | --- | --- | --- |
| | = | $Vo1/(V + dV)$, $Vw1/(V + dv)$, respectively | |
| $fx$ | = | liquid "x" fraction in batch 2 | (5) |
| | = | $dV/(V + dV)$ | |

The measured compressibilities can be expressed as:

$$bm1 = bo1 \cdot fo1 + bw1 \cdot fw1 \tag{6}$$

$$bm2 = bo2 \cdot fo2 + bw2 \cdot fw2 + bx \cdot fx \tag{7}$$

Substituting equations 1-5 into 6 and 7, yields, after rearrangement, $$bx = [bm2(1+r) - bm1]/r \tag{8}$$

$$r = dV/V \tag{9}$$

Equation 8 indicates that a value of the unknown compressibility, bx, can be determined from consecutive measurements bm1 and bm2.

Thus, if the liquid "x" is pure oil or pure water then equation (8) provides for the determination of the compressibility coefficient (bo) or (bw), as the case may be. Moreover, in determining bx, the space 41 does not have to be completely or even substantially voided of the previous sample. Thus, $r = dV/V$, can be as small as one wishes (say 0.1), keeping in mind that the accuracy of the method decreases as the value of "r" decreases. The aforementioned procedure utilizing equation (8) comprises adding and/or subtracting a measured volume of substantially pure oil or water. For subsequent accuracies on the order of one percent, pure oil or pure water can be specified as equal to, or better than, 99% water-free oil and oil-free water, respectively.

If the liquids are gassy or emulsified, samples of separated liquid can be made available by adding emulsifier materials to the liquid mixture inlet flowstream by injecting a demulsifier material through a conduit 80 by way of a control valve 82 into the conduit 14. Depending on the liquid mixture flow rate, the demulsifier will disperse throughout and partially break the emulsion. The lightest liquid, essentially water free and gassy oil, will float into the zone 24 of the space 18. Similarly, the heaviest liquid, essentially oil-free water, will settle into the space 26. Entrained gas bubbles in the oil collecting in the zone 24, may be accounted for by calculating the value of dV in equation (9) based on the gas fractions fg1, and fg2 in batches 1 and 2. Knowing the gas fraction from batch 1 and the original volume ($V_{or}$) of batch 1, determines the batch 1 liquid volume V.

$$V = V_{or}(1 - fg1) \tag{10}$$

Knowing the gas fraction fg2, and the volume of the piston stroke of the actuator 48 (dVp) determines the batch 2 liquid volume, V2

$$V2 = (V_{or} + dVp)(1 - fg2) \tag{11}$$

dV is then the difference $$dV = V2 - V = V_{or}(fg2 - fg1) - dVp(1 - fg2) \tag{12}$$

In operating the system 10 to carry out a calibration cycle, the following procedure may be used. First, the valves 42 and 44 are opened to allow fluid to flow through and flush the chamber 41. The volume of the chamber 41 may be reduced, say, about 10% by extending the piston 49 of the actuator 48 into the chamber, or, alternatively, reducing the volume of the flexible liner space if the batch sampler of U.S. Pat. No. 4,924,695 is used. The valves 42 and 44 are then closed and, for calibrating the compressibility coefficient of the oil collecting in zone 24, the valve 53 is opened and the piston of the actuator 48 is withdrawn from the chamber 41 to pull fluid through the conduit 52 into the chamber 41 to flush the conduit 52 and provide a fresh sample of oil from the zone 24. Valve 53 is then closed and valves 42 and 44 are opened to flush the chamber 41. During the flushing of chamber 41 the piston 49 is again extended into the chamber to reduce its volume by about 10% followed by closing of the valves 42 and 44 and then following by measuring the gas fraction and the compressibility of the mixture of liquid by further extending the piston 49 into the chamber to increase the pressure and "compress" the fluid in the chamber. After these measurements are taken and computed by the computer 72. the piston 49 is withdrawn sufficiently to reduce the pressure in chamber 41 to at least slightly less than that in the space 18 of the vessel 12. Valve 53 is then opened to admit a fresh sample of separated oil from the zone 24 into the chamber 41. Valve 53 is then closed and the piston 49 is again extended into the chamber 41 to increase the pressure in the space with the sample and the quantity of liquid "x" entrapped in the chamber so that the compressibility (bx) can be determined.

The above-described sequence of steps may be carried out to determine the compressibility coefficient of the water or other liquid that has collected in space 26 by evacuating stagnant fluid from the conduit 50, charging the conduit with a fresh sample of fluid and then extracting the fresh sample into the chamber 41 so that the requisite measurements are taken. Of course, the data acquisition and control system comprising the interface 70 and the computer 72 may be instructed to execute calibration cycles as often as appropriate for the particular process stream being metered through the system 10.

The gas compressibility factor Z may, in many instances, be based on a known type of gas composition and determined from existing references. The gas compressibility factor may also be obtained by empirically determining polynomial coefficients (c1, c2, c3) with which a "pseudo" compressibility factor (Z') may be expressed in terms of pressure.

$$Z' = c1 + c2P + c3PP$$

In this form Z' may be used in the simple gas equations:

$$P1V1/Z1' = P2V2/Z2'$$

Accordingly, the system 10 may be operated in a mode wherein liquid is pumped out of chamber 41 by repeated sequential opening and closing of the valves 42 and 44 while stroking the piston 49 to reduce the volume of the chamber, to pump liquid out of the chamber to completely void itself of liquids and by repeatedly admitting gas at the top of the chamber through the conduit 54 and the valve 55. Once the chamber 41 has emptied of liquid and has been progressively filled with gas, the piston 49 of the actuator 48 may be stroked into the chamber 41 to compress the gas trapped in the space and curve fit a polynomial to the pressure-volume (V, V) data as follows:

$$Z' = P(Vo - dV)/(Po, Vo) = c1 + c2P + c3PP$$

in which (Po, Vo) are initial conditions prior to the compression sequence, dV is the volume change, and P is the pressure corresponding to dV.

Figure 2:
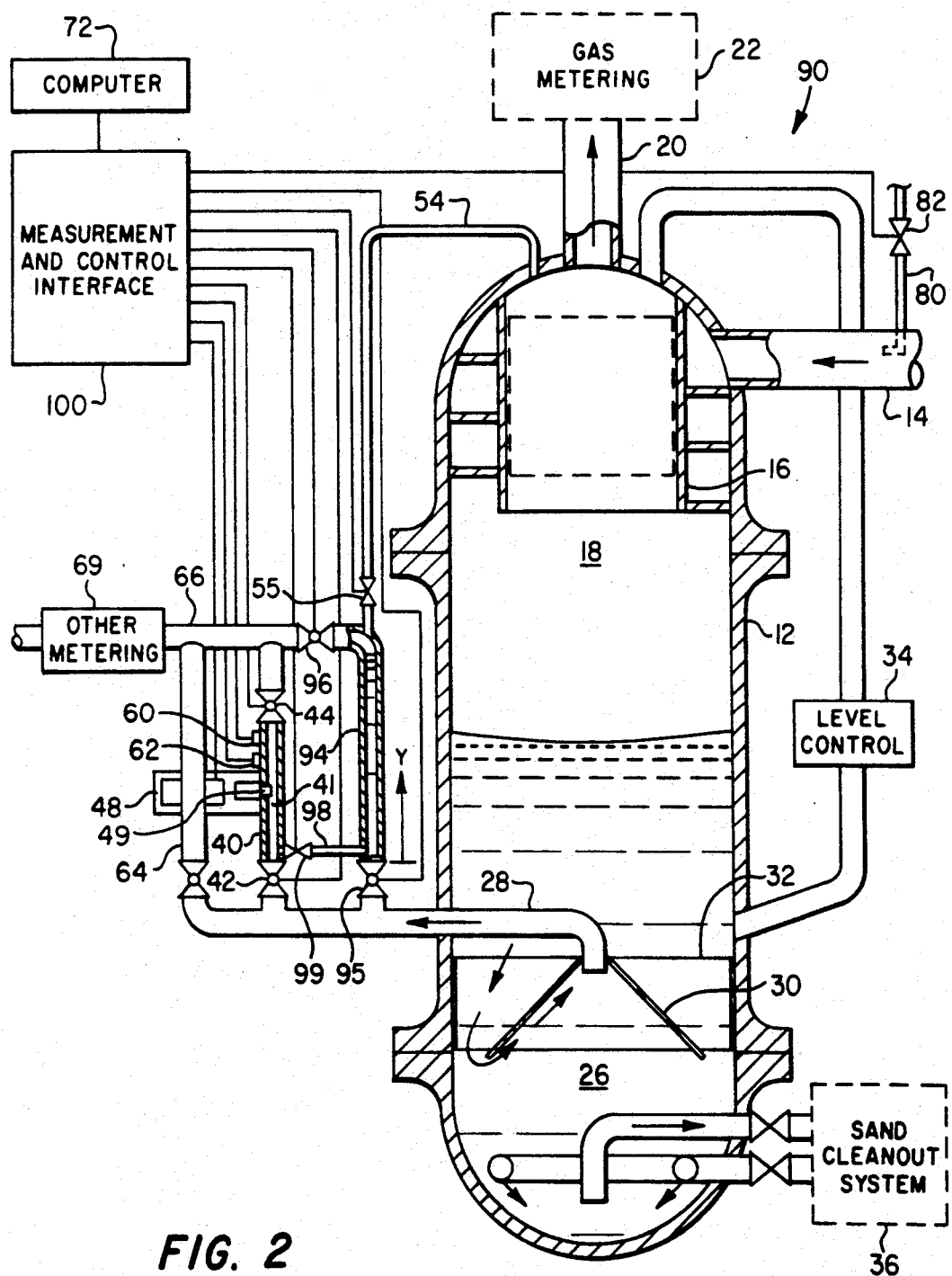
FIG. 2 is a schematic diagram of an alternate embodiment of a system in accordance with the present invention.

An alternate embodiment of a system for performing the method of the present invention is illustrated in FIG. 2. FIG. 2 illustrates a system 90 characterized by the vessel 12 with inlet and discharge conduits 14 and 28 connected thereto in the same arrangement as illustrated in FIG. 1. In fact, the major difference between the systems 10 and 90 is that, in the system 90, a generally vertically extending standpipe 94 is interconnected between the conduits 28 and 66 by remotely controllable valves 95 and 96. The standpipe 94 is also adapted to be in communication with the chamber 41 of the batch sampler 40 by way of a conduit 98 ad a remotely controllable valve 99. Instead of relying on separation of liquid in the spaces 18 and 26, liquid may be collected in the standpipe 94 between the valves 95 and 96. Accordingly, the standpipe 94 may collect a liquid sample and allow it to separate into heavier and lighter components and then periodically allow these components to be transferred to the chamber 41 for carrying out the compressibility coefficient process described hereinabove in conjunction with operation of the system 10. Instead of drawing samples of liquids from the zone 24 and the space 26 of the vessel 12 in the configuration of the system 10, selected samples of liquid are periodically withdrawn from the discharge conduit 28 into the standpipe 94, allowed to settle or separate and then incrementally metered into the chamber 41 by way of the conduit 98 and the valve 99 prior to performing the method of compressibility coefficient determination described hereinbefore. As liquid is withdrawn from the standpipe 24 through the conduit 98, the valve 55 is opened to admit gas into the space in the standpipe above the falling liquid level to make up the incremental liquid volumes that are extracted generally at the bottom of the standpipe through the conduit 98. A modified measurement and control interface 100 is operable to control the valves 42, 44, 55, 95, and 96 as well as the actuator 48 and receive measurements from the sensors 60 and 62.

Although preferred embodiments of the present invention have been described in detail herein, those skilled in the art will recognize that various substitutions and modifications may be made to the embodiments described without departing from the scope and spirit of the invention as recited in the appended claims.

What is claimed is:

1. A method for determining the compressibility of a liquid composition comprising the steps of:
   providing means for isolating a quantity of a liquid mixture to provide a first batch sample of said liquid mixture;
   determining the compressibility of said first batch sample;
   adding a predetermined volume of a liquid composition to said first batch sample to provide a second batch sample of liquid;
   determining the compressibility of said second batch sample; and
   determining the compressibility of said liquid composition based on the compressibility of said first batch sample, said second batch sample and the ratio of said predetermined volume of the liquid composition to the volume of said first batch sample.

2. The method set forth in claim 1 wherein:

compressibility of said liquid composition is determined from the equation:

$$bx = [bm2(1+r) - bm1]/r$$

where bx is the compressibility of said liquid composition, bm2 is the compressibility of the second batch sample, bm1 is the compressibility of the first batch sample, and r is the ratio of the volume of liquid composition added to the first batch sample to the volume of said first batch sample.

3. The method set forth in claim 1, including the step of:

determining the gas fraction of said first batch sample.

4. The method set forth in claim 1, including the step of:

providing means for separating said liquid mixture into a first liquid component and a second liquid component and including means for holding a quantity of said first and second liquid components, respectively; and determining the compressibility of said liquid components by withdrawing a measured quantity of said liquid components from said means for holding said liquid components, respectively and adding said liquid components as said predetermined volume to said first batch sample, respectively.

5. A method for determining the compressibility coefficient of a liquid composition comprising a component of a liquid mixture comprising the steps of:

providing means for separating said liquid mixture into at least two liquid component compositions, means for selectively receiving a predetermined quantity of liquid and at least one of said liquid components, respectively, said means for receiving including means for compressing said selected quantity of liquid and said liquid component while measuring at least one of the pressure and temperature of said selected quantity of said liquid;

conducting a flowstream of liquid mixture to said means for separating and allowing at least some of said liquid mixture to separate into said liquid components;

measuring the compressibility of said quantity of liquid;

adding an incremental volume of at least one of said liquid components to said quantity of liquid whose compressibility has been measured;

measuring the compressibility of said quantity of liquid with said liquid component added thereto; and determining the compressibility of said liquid component based on the measured compressibility of said quantity of liquid and said quantity of liquid with said liquid component added thereto and the relationship of the volume of the measured quantity of liquid and the incremental volume of said liquid component.

6. The method set forth in claim 5, including the step of:

providing said means for separating to include means for allowing said liquid mixture to separate into liquid component compositions having different densities and means for withdrawing a predetermined quantity of liquid component composition from different spaces in said means for separating.

7. The method set forth in claim 6 including the step of:

withdrawing selected quantities of liquid components from said means for separating at predetermined points in said means for separating to obtain samples of liquid of different densities.

8. A system for determining the compressibility of at least one of the liquid components of a liquid mixture, such as a mixture of oil and water, comprising:

a separator vessel including means for collecting a quantity of liquid mixture from a source and separating said liquid mixture into at least two liquid components;

means for withdrawing a portion of said liquid mixture from said vessel;

means forming a closable chamber for receiving a quantity of liquid from said vessel;

means for compressing said quantity of said liquid to decrease the volume thereof in said closable chamber;

means for introducing an incremental volume of said at least one of said liquid components into said closable chamber;

means for controlling the flow of liquid to and from said closable chamber; and means for comparing the change in volume of said liquid in said closable chamber with the pressure of said liquid in said closable chamber to determine the compressibility of said at least one of said liquid components.

9. The system set forth in claim 8 wherein:

said means for separating comprises a standpipe for receiving and holding a quantity of said liquid mixture to allow said quantity of liquid mixture to separate into said at least two liquid components; and said means for introducing said incremental volume of said at least one of said liquid components comprises a conduit interconnecting said standpipe and said means forming said closable chamber and including closable valve means interposed in said conduit.

10. The system set forth in claim 8 wherein:

said means for compressing comprises a piston actuator including piston means extendable into said closeable chamber.

* * * * *